(12) United States Patent
Shiu et al.

(10) Patent No.: US 9,549,778 B2
(45) Date of Patent: Jan. 24, 2017

(54) ADJUSTABLE TUNING OF A DIELECTRICALLY LOADED LOOP ANTENNA

(71) Applicant: COVIDIEN LP, Mansfield, MA (US)

(72) Inventors: Brian Shiu, Sunnyvale, CA (US); Kenlyn S. Bonn, Lakewood, CO (US); Mani N. Prakash, Boulder, CO (US); Tao Nguyen, Redwood City, CA (US)

(73) Assignee: COVIDIEN LP, Mansfield, MA (US)

( * ) Notice: Subject to any disclaimer, the term of this patent is extended or adjusted under 35 U.S.C. 154(b) by 313 days.

(21) Appl. No.: 14/281,344

(22) Filed: May 19, 2014

(65) Prior Publication Data

US 2014/0257267 A1    Sep. 11, 2014

Related U.S. Application Data

(63) Continuation of application No. 12/826,897, filed on Jun. 30, 2010, now Pat. No. 8,740,893.

(51) Int. Cl.
*A61B 18/18* (2006.01)
*H01Q 9/04* (2006.01)
*H01Q 9/16* (2006.01)

(52) U.S. Cl.
CPC ............ *A61B 18/1815* (2013.01); *H01Q 9/04* (2013.01); *H01Q 9/16* (2013.01); *A61B 2018/1838* (2013.01); *A61B 2018/1861* (2013.01)

(58) Field of Classification Search
CPC .............. A61B 18/1815; A61B 2018/00577; A61B 2018/183; A61B 2018/1838; A61B 2018/1861; A61B 2018/1892; A61B 2018/1853
See application file for complete search history.

(56) References Cited

U.S. PATENT DOCUMENTS

| | | | |
|---|---|---|---|
| 4,140,130 A | 2/1979 | Storm, III | |
| 4,204,549 A | 5/1980 | Paglione | |

(Continued)

FOREIGN PATENT DOCUMENTS

| | | |
|---|---|---|
| CN | 1103807 A | 6/1995 |
| DE | 390937 C | 3/1924 |

(Continued)

OTHER PUBLICATIONS

Richard Wolf Medical Instruments Corp. Brochure, "Kleppinger Bipolar Forceps & Bipolar Generator" 3 pages, Jan. 1989.

(Continued)

*Primary Examiner* — Michael Peffley (57) ABSTRACT

A microwave antenna assembly is disclosed. The antenna assembly includes an elongated member defining a longitudinal axis and having proximal and distal ends. The antenna assembly also includes an outer conductor and an inner conductor each disposed within the elongated member and extending along the longitudinal axis. A portion of the inner conductor is deployable relative to the outer conductor such that the antenna assembly may transition from a first configuration to a second configuration. The antenna assembly also includes an expandable sheath at least partially disposed about a distal portion of the inner conductor and defining at one or more lumens configured to couple to a supply of dielectric material used to regulate the expansion of the expandable sheath.

20 Claims, 7 Drawing Sheets

(56) References Cited

U.S. PATENT DOCUMENTS

| | | |
|---|---|---|
| D263,020 S | 2/1982 | Rau, III |
| 4,462,412 A | 7/1984 | Turner |
| 4,632,128 A | 12/1986 | Paglione et al. |
| 4,658,836 A | 4/1987 | Turner |
| D295,893 S | 5/1988 | Sharkany et al. |
| D295,894 S | 5/1988 | Sharkany et al. |
| 4,825,880 A | 5/1989 | Stauffer et al. |
| 4,934,365 A | 6/1990 | Morgenthaler |
| 4,945,912 A | 8/1990 | Langberg |
| 4,974,587 A | 12/1990 | Turner et al. |
| 5,057,106 A | 10/1991 | Kasevich et al. |
| 5,097,846 A | 3/1992 | Larsen |
| 5,246,438 A | 9/1993 | Langberg |
| 5,354,325 A | 10/1994 | Chive et al. |
| 5,370,644 A | 12/1994 | Langberg |
| 5,405,346 A | 4/1995 | Grundy et al. |
| 5,599,295 A | 2/1997 | Rosen et al. |
| 5,693,082 A | 12/1997 | Warner et al. |
| 5,720,718 A | 2/1998 | Rosen et al. |
| 5,800,494 A | 9/1998 | Campbell et al. |
| 5,810,803 A | 9/1998 | Moss et al. |
| 5,904,709 A | 5/1999 | Arndt et al. |
| 5,957,969 A | 9/1999 | Warner et al. |
| 5,961,871 A | 10/1999 | Bible et al. |
| 6,047,216 A | 4/2000 | Carl et al. |
| D424,694 S | 5/2000 | Tetzlaff et al. |
| D425,201 S | 5/2000 | Tetzlaff et al. |
| 6,067,475 A | 5/2000 | Graves et al. |
| 6,134,476 A | 10/2000 | Arndt et al. |
| 6,175,768 B1 | 1/2001 | Arndt et al. |
| 6,208,903 B1 | 3/2001 | Richards et al. |
| 6,223,086 B1 | 4/2001 | Carl et al. |
| 6,226,553 B1 | 5/2001 | Carl et al. |
| 6,230,060 B1 | 5/2001 | Mawhinney |
| 6,245,062 B1 | 6/2001 | Berube et al. |
| 6,289,249 B1 | 9/2001 | Arndt et al. |
| D449,886 S | 10/2001 | Tetzlaff et al. |
| 6,312,427 B1 | 11/2001 | Berube et al. |
| 6,325,796 B1 | 12/2001 | Berube et al. |
| 6,334,074 B1 | 12/2001 | Spertell |
| 6,350,276 B1 | 2/2002 | Knowlton |
| 6,364,876 B1 | 4/2002 | Erb et al. |
| D457,958 S | 5/2002 | Dycus et al. |
| D457,959 S | 5/2002 | Tetzlaff et al. |
| 6,383,182 B1 | 5/2002 | Berube et al. |
| 6,496,736 B1 | 12/2002 | Carl et al. |
| 6,496,738 B2 | 12/2002 | Carr |
| 6,512,956 B2 | 1/2003 | Arndt et al. |
| 6,592,579 B2 | 7/2003 | Arndt et al. |
| 6,675,050 B2 | 1/2004 | Arndt et al. |
| 6,723,091 B2 | 4/2004 | Goble et al. |
| D496,997 S | 10/2004 | Dycus et al. |
| D499,181 S | 11/2004 | Dycus et al. |
| 6,847,848 B2 | 1/2005 | Sterzer et al. |
| 6,962,586 B2 | 11/2005 | Berube et al. |
| D525,361 S | 7/2006 | Hushka |
| 7,101,369 B2 | 9/2006 | van der Welde |
| D531,311 S | 10/2006 | Guerra et al. |
| 7,115,126 B2 | 10/2006 | Berube et al. |
| 7,118,590 B1 | 10/2006 | Cronin |
| D533,942 S | 12/2006 | Kerr et al. |
| D535,027 S | 1/2007 | James et al. |
| 7,197,363 B2 * | 3/2007 | Prakash .......... A61B 18/18 606/33 |
| D541,418 S | 4/2007 | Schechter et al. |
| D541,938 S | 5/2007 | Kerr et al |
| 7,226,446 B1 | 6/2007 | Mody et al. |
| 7,300,436 B2 | 11/2007 | Penny et al. |
| 7,311,703 B2 * | 12/2007 | Turovskiy .......... A61B 18/18 606/33 |
| D564,662 S | 3/2008 | Moses et al. |
| 7,387,627 B2 | 6/2008 | Erb et al. |
| 7,642,451 B2 | 1/2010 | Bonn |
| D613,412 S | 4/2010 | DeCarlo |
| 8,740,893 B2 | 6/2014 | Shiu et al. |
| 2002/0087151 A1 | 7/2002 | Mody et al. |
| 2003/0109868 A1 | 6/2003 | Chin et al. |
| 2005/0149010 A1 | 7/2005 | Turovskiy et al. |
| 2005/0203388 A1 | 9/2005 | Carr |
| 2005/0240239 A1 | 10/2005 | Boveja et al. |
| 2005/0245919 A1 | 11/2005 | van der Welde |
| 2006/0085054 A1 | 4/2006 | Zikorus et al. |
| 2006/0116673 A1 | 6/2006 | Gauthier et al. |
| 2006/0293651 A1 | 12/2006 | Cronin |
| 2006/0293652 A1 | 12/2006 | van der Weide |
| 2007/0043346 A1 | 2/2007 | Cronin |
| 2007/0191825 A1 | 8/2007 | Cronin et al. |
| 2007/0203480 A1 | 8/2007 | Mody et al. |
| 2007/0203551 A1 | 8/2007 | Cronin et al. |
| 2007/0282319 A1 | 12/2007 | van der Weide et al. |
| 2007/0299488 A1 | 12/2007 | Carr |
| 2008/0068485 A1 | 3/2008 | Yuyama |
| 2009/0076492 A1 | 3/2009 | Behnke |
| 2009/0131926 A1 | 5/2009 | Rusin et al. |
| 2009/0183895 A1 | 7/2009 | Bonn |
| 2009/0295674 A1 | 12/2009 | Bonn |
| 2010/0049185 A1 | 2/2010 | Paulus |
| 2010/0101825 A1 | 4/2010 | Bonn |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 836 868 A2 | 4/1998 |
| EP | 0 882 955 A1 | 12/1998 |
| EP | 1 159 926 A2 | 12/2001 |
| EP | 1186274 | 4/2006 |
| EP | 2128929 A1 | 12/2009 |
| FR | 179 607 | 11/1906 |
| FR | 1 275 415 A | 11/1961 |

(56) References Cited

FOREIGN PATENT DOCUMENTS

| | | |
|---|---|---|
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| GB | 2434872 A | 8/2007 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 2004/112628 A1 | 12/2004 |
| WO | 2005/011049 A2 | 2/2005 |
| WO | 2007/076924 A2 | 7/2007 |
| WO | 2007112081 A1 | 10/2007 |
| WO | 2008068486 A2 | 6/2008 |
| WO | 2010/035831 A1 | 4/2010 |

OTHER PUBLICATIONS

Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.

(56) References Cited

OTHER PUBLICATIONS

European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
U.S. Appl. No. 12/696,966, filed Jan. 29, 2010.
U.S. Appl. No. 12/701,030, filed Feb. 5, 2010.
U.S. Appl. No. 12/708,974, filed Feb. 19, 2010.
U.S. Appl. No. 12/709,014, filed Feb. 19, 2010.
U.S. Appl. No. 12/712,864, filed Feb. 25, 2010.
U.S. Appl. No. 12/713,429, filed Feb. 26, 2010.
U.S. Appl. No. 12/713,515, filed Feb. 26, 2010.
U.S. Appl. No. 12/713,641, filed Feb. 26, 2010.
U.S. Appl. No. 12/722,034, filed Mar. 11, 2010.
U.S. Appl. No. 12/731,367, filed Mar. 25, 2010.
U.S. Appl. No. 12/732,508, filed Mar. 26, 2010.
U.S. Appl. No. 12/732,521, filed Mar. 26, 2010.
U.S. Appl. No. 12/761,267, filed Apr. 15, 2010.
U.S. Appl. No. 12/769,457, filed Apr. 28, 2010.
U.S. Appl. No. 12/772,675, filed May 3, 2010.
U.S. Appl. No. 12/777,984, filed May 11, 2010.
U.S. Appl. No. 12/786,671, filed May 25, 2010.
U.S. Appl. No. 12/787,639, filed May 26, 2010.
U.S. Appl. No. 12/792,904, filed Jun. 3, 2010.
U.S. Appl. No. 12/792,932, filed Jun. 3, 2010.
U.S. Appl. No. 12/792,947, filed Jun. 3, 2010.
U.S. Appl. No. 12/792,970, filed Jun. 3, 2010.
U.S. Appl. No. 12/793,037, filed Jun. 3, 2010.
U.S. Appl. No. 12/819,330, filed Jun. 21, 2010.
U.S. Appl. No. 12/823,211, filed Jun. 25, 2010.
Alexander et al., "Magnetic Resonance Image-Directed Stereotactic Neurosurgery; Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With no Moving Parts", Nov. 1, 2003; 4 pages.
Geddes et al., "The Measurement of Physiologic Events by Electrical Impedence" Am. J. MI, Jan. Mar. 1964, pp. 16-27.

(56) References Cited

OTHER PUBLICATIONS

Goldberg et al., "Image-guided Radiofrequency Tumor Ablation: Challenges and Opportunities—Part I", (2001) J Vasc. Interv. Radio, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/423,609, filed Apr. 14, 2009.
U.S. Appl. No. 12/436,231, filed May 6, 2009.
U.S. Appl. No. 12/436,237, filed May 6, 2009.

(56) References Cited

OTHER PUBLICATIONS

U.S. Appl. No. 12/436,239, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/556,238, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,323, filed Nov. 16, 2009.
U.S. Appl. No. 12/619,462, filed Nov. 16, 2009.
U.S. Appl. No. 12/620,289, filed Nov. 17, 2009.
U.S. Appl. No. 12/642,623, filed Dec. 18, 2009.
U.S. Appl. No. 12/686,726, filed Jan. 13, 2010.
U.S. Appl. No. 12/692,856, filed Jan. 25, 2010.
U.S. Appl. No. 12/696,671, filed Jan. 29, 2010.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.

\* cited by examiner

12,826,897, filed on Jun. 30, now U.S. Pat. No. 8,740,893, the disclosure entire contents of which are incorporated herein by reference.

ADJUSTABLE TUNING OF A DIELECTRICALLY LOADED LOOP ANTENNA

CROSS-REFERENCE TO RELATED APPLICATIONS

The present application is a continuation application of U.S. patent application Ser. No. 12/826,897 filed on Jun. 30, 2010, now U.S. Pat. No. 8,740,893, the disclosure entire contents of which are incorporated herein by reference.

BACKGROUND

1. Technical Field

The present disclosure relates generally to microwave antennas. More particularly, the present disclosure is directed to flexible loop antenna having a variable dielectric loading.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

SUMMARY

According to one embodiment of the present disclosure, a microwave antenna assembly is disclosed. The antenna assembly includes an elongated member defining a longitudinal axis and having proximal and distal ends. The antenna assembly also includes an outer conductor and an inner conductor each disposed within the elongated member and extending along the longitudinal axis. A portion of the inner conductor is deployable relative to the outer conductor such that the antenna assembly may transition from a first configuration to a second configuration. The antenna assembly also includes an expandable sheath at least partially disposed about a distal portion of the inner conductor and defining at least one lumen configured to couple to a supply of dielectric material used to selectively expand the sheath.

According to another embodiment of the present disclosure, a microwave ablation system is disclosed. The system includes an antenna assembly having an elongated member defining a longitudinal axis and having proximal and distal ends. The antenna assembly also includes an outer conductor and an inner conductor each disposed within the elongated member and extending along the longitudinal axis. A portion of the inner conductor is deployable relative to the outer conductor such that the antenna assembly may transition from a first configuration to a second configuration. The antenna assembly also includes an expandable sheath at least partially disposed about a distal portion of the inner conductor and defining at least one lumen configured to receive a dielectric material. The system includes a fill source coupled to the lumen and configured to regulate the amount of the dielectric material within the lumen to control the expansion of the expandable sheath.

A method for performing microwave ablation is also contemplated by the present disclosure. The method includes the initial step of inserting an antenna assembly into a tissue volume. The antenna assembly includes an outer conductor, an inner conductor and an expandable sheath at least partially disposed about a distal portion of the inner conductor and defining at least one lumen. The method also includes the steps of deploying at least a portion of the inner conductor from the outer conductor such that the antenna assembly may transition from a first configuration to a second configuration and regulating an amount of a dielectric material supplied to the at least one lumen to control expansion of the expandable sheath. The method further includes the steps of energizing the antenna assembly to ablate the tissue volume and withdrawing the dielectric material from the at least one lumen to deflate the expandable sheath.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described herein below with reference to the accompanying drawings. In the following description, well-known functions or constructions are not described in detail to avoid obscuring the present disclosure in unnecessary detail. In the drawings and in the description that follows, the term "proximal," as is traditional, will refer to the end of the apparatus that is closest to the clinician, while the term "distal" will refer to the end that is furthest from the clinician.

Figure 1:
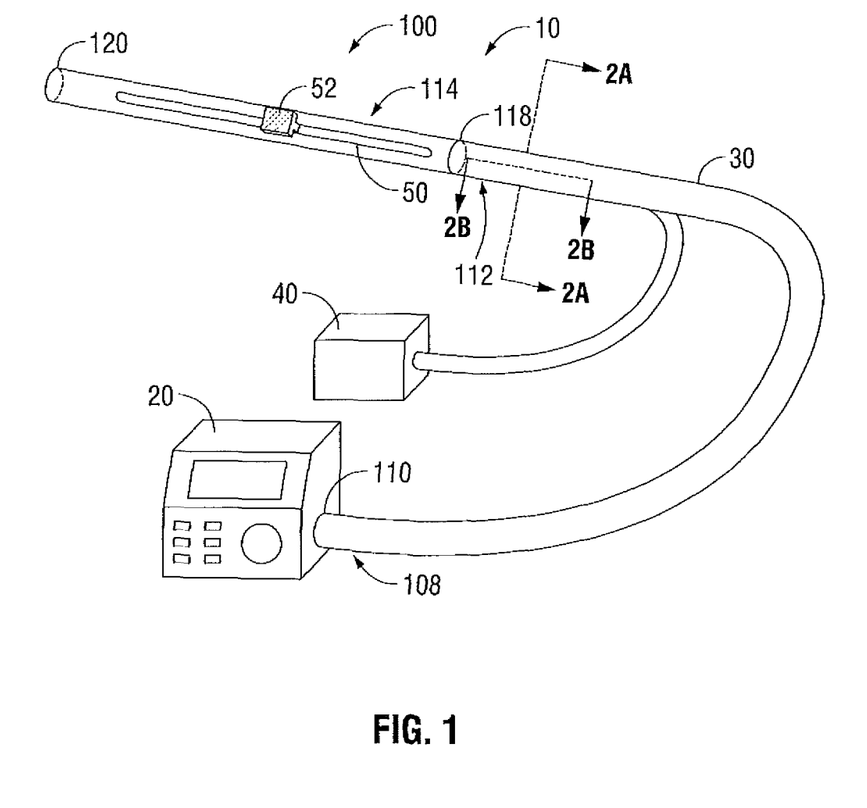
FIG. 1 is a perspective view of a microwave ablation system according to an embodiment of the present disclosure.

Referring to FIG. 1, a microwave tissue treatment system 10 in accordance with an embodiment of the present disclosure is shown. System 10 includes a microwave antenna assembly 100 connected to a power source or supply 20, e.g., a microwave or RF generator or any suitable power generating device suitable for energizing the antenna assembly 100, through a feedline 30. The power supply 20 is configured to provide microwave energy at an operational frequency from about 300 MHz to about 10,000 MHz.

The system 10 also includes a fill source 40, e.g., an electric motor pump, a peristaltic pump or the like, as a mechanism for circulating a dielectric material "M," such as gas (e.g., nitrogen, air, etc.) or liquid (e.g., saline, water, etc.) through the antenna assembly 100, as described below. Antenna assembly 100 may further include a pusher or deployment assembly 50 that includes a deployment knob 52 operatively engaged with or coupled to the antenna assembly 100, as described in further detail below.

Figure 2A:
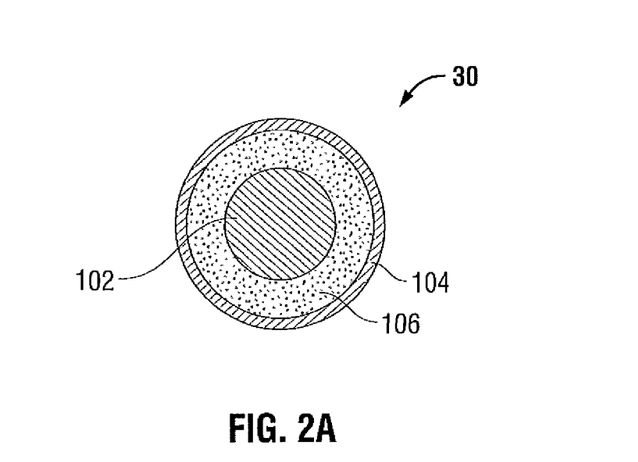
FIGS. 2A-2B are cross-sectional views of a feedline according to an embodiment of the present disclosure.
Figure 2B:
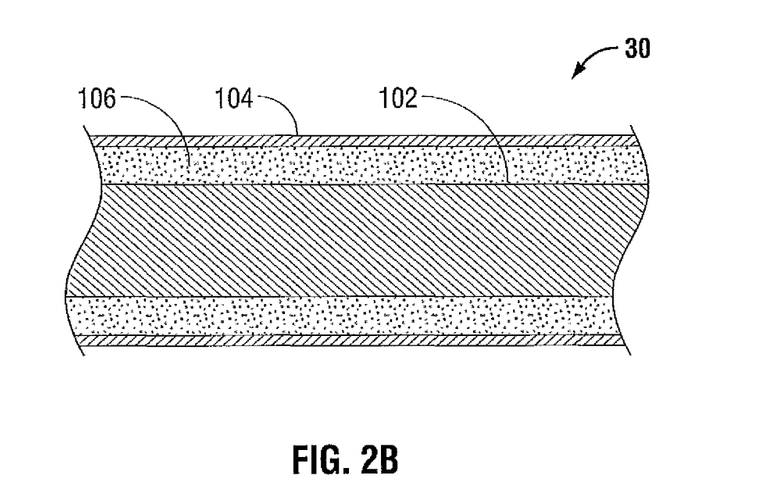

Referring now to FIGS. 1-2B, as indicated above, antenna assembly 100 is electrically connected to generator or power supply 20 by feedline 30. Feedline 30 may be any suitable conductive pathway capable of transferring an electrical current to antenna assembly 100. In one embodiment, as seen in FIGS. 2A-2B, feedline 30 may be a coaxial cable composed of an inner conductor 102, an outer conductor 104, and an inner insulator 106 interposed between inner and outer conductors 102, 104 to electrically separate and/or isolate inner and outer conductors 102,104 from one another. Inner and outer conductors 102, 104 may each be made of a suitable conductive material that may be semi-rigid or flexible, while inner insulator 106 may include any number of suitable non-conductive materials such as ceramic and polytetrafluoroethylene (PTFE). Inner and outer conductors 102, 104 of feedline 30 may incorporate any suitable conductive material or metal, including, but not limited to, silver, copper and gold. In certain embodiments, inner and outer conductors 102, 104 of feedline 30 may include a conductive or non-conductive substrate plated or coated with a suitable conductive material. The inner conductor and outer conductor 104 may be constructed of copper, gold, stainless steel or other conductive metals with similar conductivity values.

Feedline 30 may range in length from about 1 foot (0.3048 m) to about 15 feet (4.572 m), or greater depending on a particular application. In one embodiment, the feedline 30 may be formed from a coaxial, semi-rigid or flexible cable having a wire with a 0.047" outer diameter rated for 50 Ohms. As depicted in FIG. 1, feedline 30 has a proximal portion 108 operatively connected to, or connectable to, power supply 20 at proximal end 110, and a distal portion 112 that forms a part of microwave antenna assembly 100, as disclosed below. In some embodiments, the feedline 30 and power supply 20 may be a part of an integrated handheld device.

Referring now to FIGS. 1, 3-5, the antenna assembly 100 includes an elongated member 114 disposed about the distal portion 112 of feedline 30, and a sheath 116 that at least partially surrounds a distal portion 102a (FIG. 3) of the inner conductor 102, as described in further detail below. Elongated member 114 has proximal and distal ends 118, 120 and defines longitudinal axis "A." Elongated member 114 may be formed of any material suitable for electrically insulating a clinician or operator from the inner and outer conductors 102, 104 of feedline 30 disposed therein such that the antenna assembly 100 may be handled during use.

In non-deployed configuration, the elongated member 114 conceals a distal portion 102a (FIG. 3) of the inner conductor 102 when the microwave antenna assembly 100 is not in use so as to prevent unintentional damage or injury. In particular, the elongated member 114 conceals the distal portion 112 of feedline 30, which includes distal portions 102a, 104a, and 106a of the inner conductor 102, the outer conductor 104, and the inner insulator 106, respectively. Accordingly, the inner conductor 102, the outer conductor 104, and the inner insulator 106 also constitute components of antenna assembly 100.

At least a portion of the inner conductor 102, i.e. distal portion 102a, is deployable relative to distal portion 104a of the outer conductor, such that the antenna assembly 100 may transition from a first, non-deployed configuration (FIG. 3), to a second, deployed configuration during use (FIGS. 4 and 5), as described in further detail below. In the first condition, the distal portion 102a of the inner conductor is at least partially disposed within the distal portion 104a of the outer conductor and the elongated member 114. In the second, deployed configuration, the distal portion 102a of the inner conductor extends at least partially beyond a distal end 120 of elongated member 114, such that contact may be made with the target tissue.

Movement from the first configuration to the second configuration may be facilitated through the use of any suitable mechanism, such as, for example, a deployment assembly 50 (FIG. 1). Reference may be made to commonly-owned U.S. Patent Publication No. 2004/0267156, filed Apr. 4, 2004, for a detailed discussion regarding the components and functionality of deployment assembly 50, the entire contents of which is incorporated herein.

Figure 4:
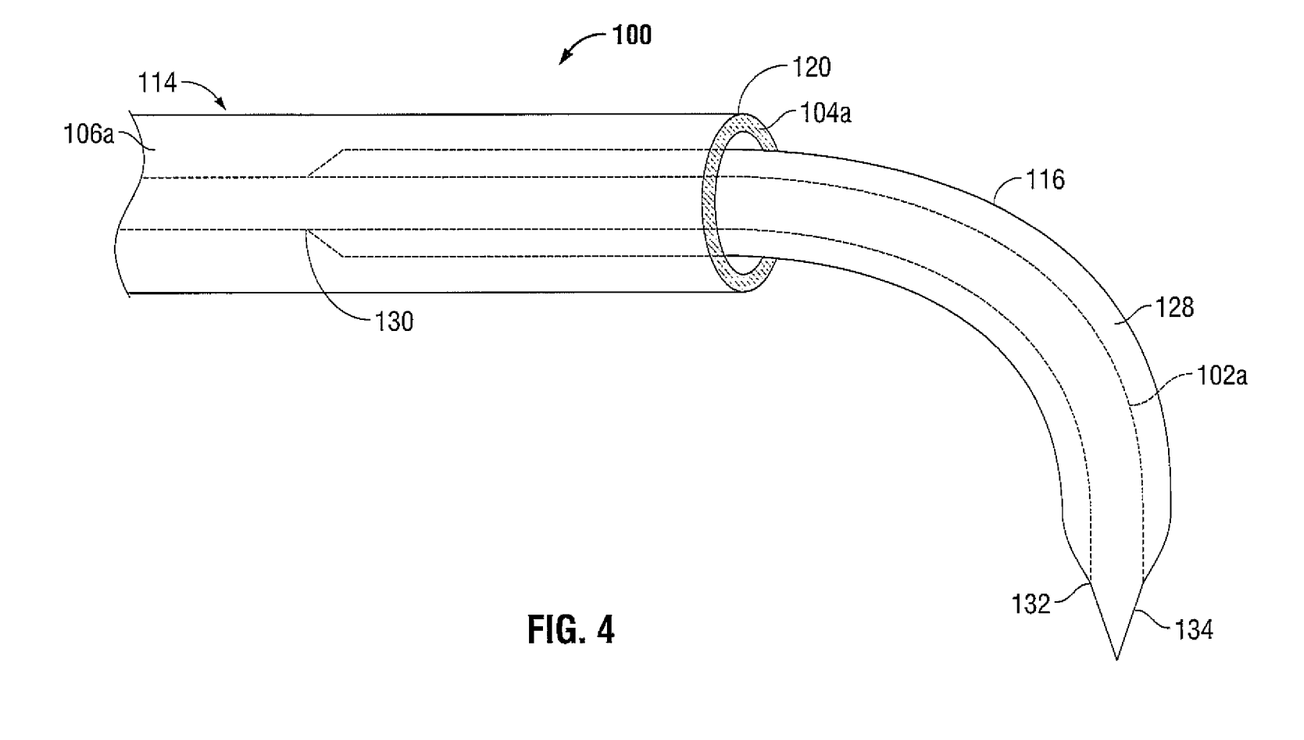
FIG. 4 is a partial, cross-sectional view of the microwave antenna assembly of FIG. 2 in a partially deployed configuration according to an embodiment of the present disclosure.

In one embodiment, as seen in FIG. 4, antenna assembly 100 includes a distal portion 102a of an inner conductor that exhibits a substantially arcuate or curved profile when deployed. FIG. 4 shows the antenna assembly 100 in a partially deployed configuration. Reference may be made to commonly-owned U.S. Pat. No. 7,197,363 for a detailed discussion of the structure of arcuate microwave antenna configurations, the entire contents of which is incorporated herein.

Figure 3:
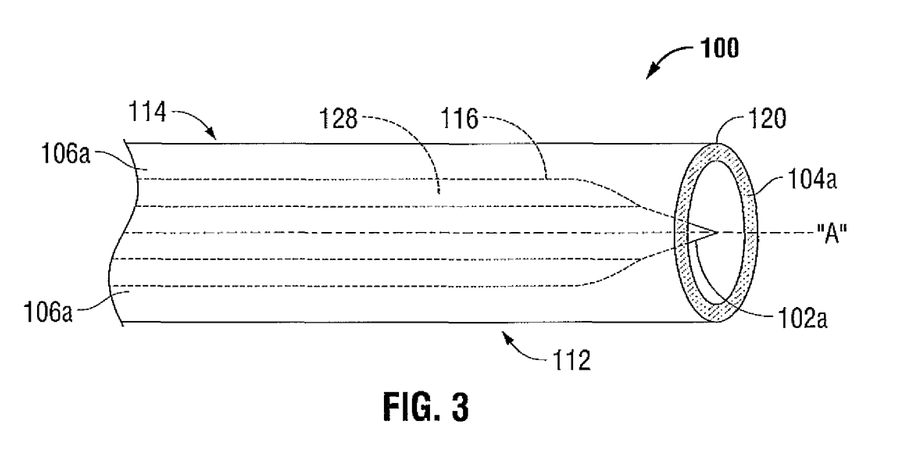
FIG. 3 is a partial, cross-sectional view of a microwave antenna assembly according to an embodiment of the present disclosure.

With continued reference to FIGS. 3 and 4, the sheath 116 is disposed about distal portion 102a of the inner conductor in such a manner so as to define a lumen 128. Sheath 116 may be fixedly, releasably, or slidably connected to distal portion 102a in any suitable manner including, but not being limited to, welding or adhering, as would be appreciated by one skilled in the art. Sheath 116 has proximal and distal ends 130, 132 defined by the points at which sheath 116 is connected to distal portion 102a. In one embodiment, as best seen in FIG. 4, the distal-most tip 134 of distal portion 102a extends beyond the distal end 132 of sheath 116. In another embodiment, the sheath 116 may be connected to the distal portion 102a of an inner conductor 102 at the distal-most tip 132 thereof, or at a point therebeyond (not shown).

The proximal end 130 of sheath 116 may be located at any suitable location along the length of distal portion 102a of the inner conductor, dependent upon the desired volume of lumen 128. Although depicted as substantially incisive, the present disclosure contemplates that distal-most tip 134 may be substantially arcuate, duckbilled, or any other such configuration suitable for facilitating the entry of the microwave tissue treatment device into the tissue of a patient.

Sheath 116 may be formed of any suitable biocompatible, impermeable material capable of retaining gas and/or fluid therein, including and not limited to PTFE and tetrafluor-ethylene-perfluorpropylene (FEP). The present disclosure contemplates that sheath 116 may be either substantially rigid, or substantially non-rigid in character.

Referring back to FIG. 1, the fill source 40 operates in conjunction with, and is fluidly connected to, lumen 128 of sheath 116 such that one or more dielectric materials (e.g., fluids or gases) may be circulated therethrough. The dielectric compounds also serve to dissipate some of the heat generated by the antenna assembly during use in addition to acting as a medium that modifies the dielectric constant of the distal portion of the antenna assembly. Suitable dielectric fluids include, but are not limited to, water, saline, liquid chlorodifluoromethane, or any suitable perfluorocarbon fluid, such as Fluorinert®, distributed commercially by Minnesota Mining and Manufacturing Company (3M™), St. Paul, Minn., USA. Suitable dielectric gases include air, nitrogen, nitrous oxide, carbon dioxide and the like. In yet another variation, a combination of liquids and/or gases may be utilized. The compounds circulated through the lumen 128 may vary depending upon the desired cooling rate and the desired tissue impedance matching properties. The fill source 40 includes a suitable pump configured to supply the dielectric material "M" to the lumen 128. If fluid is being used, the pump may be any type of peristaltic pump and the like. If gas is being used, any type of electric gas pump or compressor may be utilized.

Figure 5:
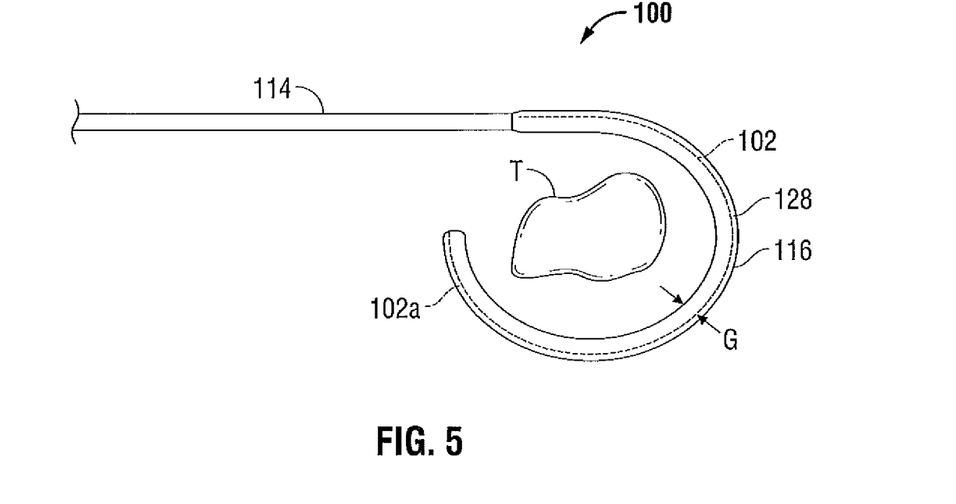
FIG. 5 is a top view of the microwave antenna assembly of FIG. 2 in a fully deployed configuration according to an embodiment of the present disclosure.

FIG. 5 shows the antenna assembly 100 in a fully deployed configuration, in which the inner conductor 102 fully encompasses a tissue volume "T" targeted for ablation. The inner conductor 102 is formed from a flexible metal suitable to curve about the tissue volume "T" such that the produced ablation volume when the inner conductor 102 is energized by the microwave energy encompasses the tissue volume "T." The inner conductor 102 may be made from a shape memory alloy, e.g., Nitinol or some other similar alloy, such that as distal portion 102a is inserted within the tissue, the distal portion 102a may form the curved and/or helical shape about the tissue volume "T" within the formed ablation volume. The inner conductor 102 extends laterally in relation to the longitudinal axis "A" to define an ablation region that surrounds the tissue volume "T" to be treated in such a manner that the tissue volume "T" is located within the ablation region.

In one embodiment, the inner conductor may be formed from a 0.022" Nitinol wire and the sheath 116 may be formed from PTFE sleeve having an inner diameter of about 0.022" and an outer diameter of about 0.050." The sheath 116 may be inflated using the fill source 40 to adjust the dielectric properties along the length of the inner conductor 102. The sheath 116 may be in a deflated state during the deployment of inner conductor 102 within the tissue. Once inner conductor 102 has been desirably positioned, sheath 106 may be filled with the desired dielectric material "M," until the sheath 116 has inflated sufficiently about the inner conductor 102. The size of inflated sheath 116 may be varied according to the desired radiative effects, the length of deployed inner conductor 102, as well as the type of tissue.

Figure 6:
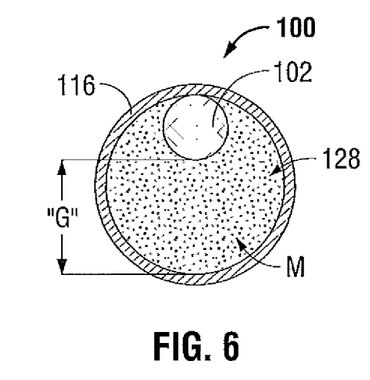
FIG. 6 is a cross-sectional view of the microwave antenna assembly of FIG. 5 according to an embodiment of the present disclosure.

FIG. 6 shows the cross-sectional view of the antenna assembly 100. The dielectric material "M" is supplied to the lumen 128 to provide a dielectric gap "G" between the inner conductor 102 and the sheath 116. The antenna assembly 100 may be curved, as shown in FIG. 5, to position the gap "G" toward the center of curved antenna assembly 100.

In one embodiment, the lumen 128 may be filled with any dielectric material "M" having a relatively low dielectric permittivity as compared to the material forming the sheath 116. In another embodiment, the lumen 128 may be filled with air, since air has a dielectric constant of 1. A lower dielectric permittivity within the lumen 128 allows for microwave energy to travel through the gap "G" easier than through the sheath 116. Therefore, positioning of the inner conductor 102 in contact with the sheath 116 (e.g., off-center) and curving the antenna assembly 100 such that the gap "G" is facing toward the center of the curved antenna assembly 100 directs the microwave energy toward the center of the looped antenna assembly 100. In particular, this configuration of the gap "G" directs the microwave energy into the looped antenna assembly 100 more efficiently along the inside thereof as opposed to the outside. In other words, this configuration maximizes matching toward the center of the curved inner conductor 102, allowing for better microwave transmission, thereby maximizing ablation within the inner conductor 102. Conversely, this configuration minimizes effects outside the curved inner conductor 102, since the dielectric material "M" of the sheath 116 limits microwave transmission and provides for poor impedance matching between the tissue and the antenna assembly 100.

Figure 7:
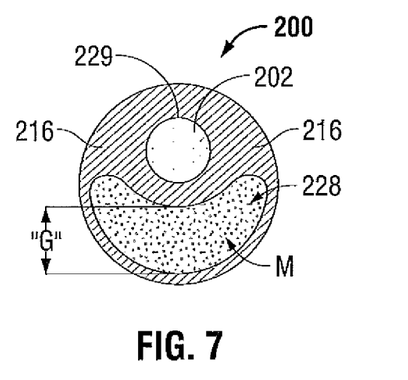
FIG. 7 is a cross-sectional view of another embodiment of a microwave antenna assembly according to an embodiment of the present disclosure.

FIG. 7 shows another embodiment of an antenna assembly 200 having an inner conductor 202 disposed within a multi-lumen sheath 216. The antenna assembly 200 may be curved in a similar manner as the antenna assembly 100 as shown in FIG. 5. The sheath 216 includes two or more lumens 228 and 229 defined therein. The multi-lumen configuration allows for first lumen 228 to provide for a dielectric gap "G" between the inner conductor 202 and the sheath 216 and the inner conductor 202 to be disposed within the second lumen 229. Multi-lumen structure allows for molding of the first lumen 228 to achieve a predetermined shape of the dielectric gap "G" suitable for directing microwave energy into the center of the curved inner conductor 202.

Figure 8:
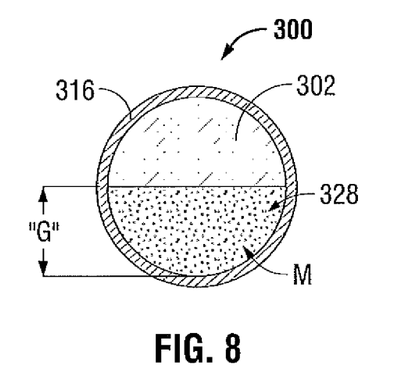
FIG. 8 is a cross-sectional view of another embodiment of a microwave antenna assembly according to an embodiment of the present disclosure.

FIG. 8 shows a further embodiment of an antenna assembly 300 having an inner conductor 302 disposed within a sheath 316 having a lumen 328 defined therein. The antenna assembly 300 may be curved in a similar manner as the antenna assembly 100 as shown in FIG. 5. The inner conductor 302 has a substantially hemi-spherical cross-section. This geometry subdivides the lumen 328 to form a dielectric gap "G" between the inner conductor 302 and the sheath 316.

Figure 9:
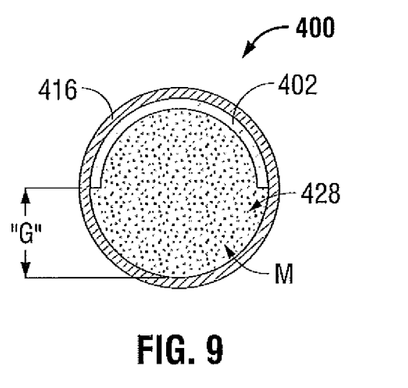
FIG. 9 is a cross-sectional view of another embodiment of a microwave antenna assembly according to an embodiment of the present disclosure.

FIG. 9 also shows another embodiment of an antenna assembly 400 having an inner conductor 402 of different geometries. The antenna assembly 400 may be curved in a similar manner as the antenna assembly 100 as shown in FIG. 5. The inner conductor 402 has a substantially U-shaped cross-section. This geometry also subdivides the lumen 428 to form a dielectric gap "G" between the inner conductor 402 and the sheath 416.

The cross-sectional shape of the inner conductors 302 and 402 provide for an enhanced dielectric gap "G." In particular, the shape of the inner conductors 302 and 402 in combination with the enhanced dielectric gaps "G" provide for directed deposition of microwave energy toward the center of the curved antenna assemblies 300 and 400. In other words, these configurations direct the microwave energy more efficiently along the inside thereof as opposed to the outside.

Figure 10:
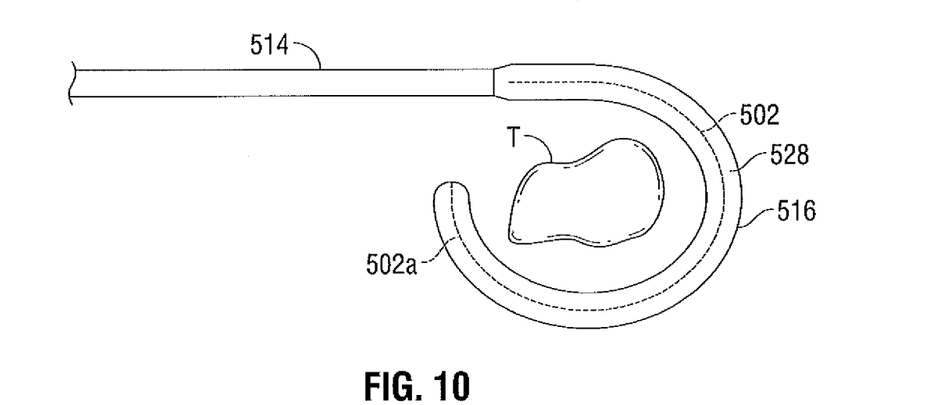
FIG. 10 is a top view of a microwave antenna assembly in a fully deployed configuration according to an embodiment of the present disclosure.
Figure 11:
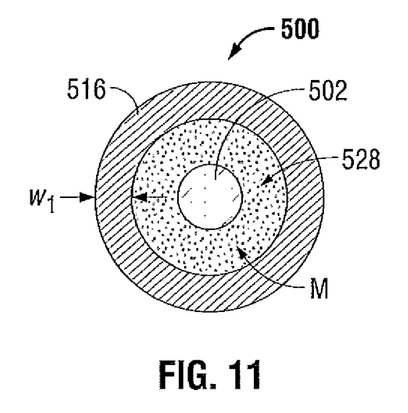
FIG. 11 is a cross-sectional view of the microwave antenna assembly of FIG. 10 in a deflated configuration according to an embodiment of the present disclosure.
Figure 12:
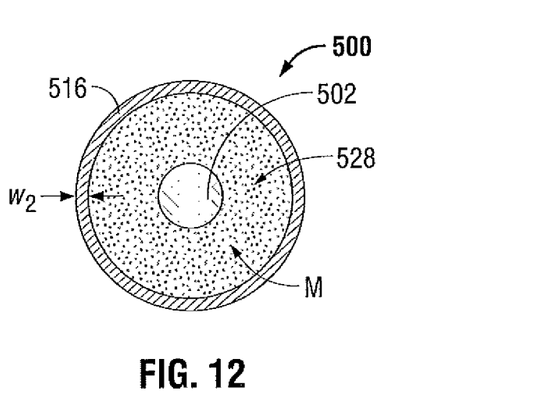
FIG. 12 is a cross-sectional view of the microwave antenna assembly of FIG. 10 in an inflated configuration according to an embodiment of the present disclosure.

FIGS. 10-12 show another embodiment of the antenna assembly 500. The antenna assembly 500 includes an elongated member 514 disposed about the distal portion 112 of feedline 30 (FIG. 1), and a sheath 516 that at least partially surrounds a distal portion 502a of an inner conductor 502. The elongated member 514 is substantially similar to the elongated member 114 and may also be formed of any material suitable for electrically insulating a clinician or operator from the inner conductor 502 disposed therein such that the antenna assembly 500 may be handled during use. The inner conductor 502 may be deployed from within the elongated member 514 similar to the inner conductor 102 as discussed above with respect to FIGS. 3-5.

FIG. 10 shows the antenna assembly 500 in a fully deployed configuration, in which the inner conductor 502 fully encompasses a tissue volume "T" targeted for ablation. The inner conductor 502 is formed from a flexible metal suitable to curve about the tissue volume "T" such that the produced ablation volume when the inner conductor 502 is energized by the microwave energy encompasses the tissue volume "T." The inner conductor 502 may be made from a shape memory alloy, e.g., Nitinol or some other similar alloy, such that as distal portion 502a is inserted within the tissue, it may be preconfigured to form the curved shape as the inner conductor 502 is further inserted within the tissue.

The sheath 516 at least partially surrounds the distal portion 502a of the inner conductor 502 and defines a lumen 528 thereabout. The sheath 516 may be fixedly, releasably, or slidably connected to distal portion 502a in any suitable manner including, but not being limited to, welding or adhering, as would be appreciated by one skilled in the art. The sheath 516 may be formed of any suitable biocompatible, impermeable material capable of retaining gas and/or fluid therein, including, but not limited to, PTFE and tetra-fluorethylene-perfluorpropylene (FEP).

The sheath 516 is formed from a flexible expandable material, such that during inflation, the sheath 516 expands to accommodate the increased volume of the dielectric material "M." The lumen 528 is in fluid communication with the fill source 40 such that one or more dielectric materials (e.g., fluids or gases) may be circulated therethrough, which are used to inflate the sheath 516.

Suitable dielectric fluids include, but are not limited to, water, saline, liquid chlorodifluoromethane, or any suitable perfluorocarbon fluid, such as Fluorinert®, distributed commercially by Minnesota Mining and Manufacturing Company (3M™), St. Paul, Minn., USA. Suitable dielectric gases include air, nitrogen, nitrous oxide, carbon dioxide and the like. In yet another variation, a combination of liquids and/or gases may be utilized. The selection of dielectric mixtures may be used to provide for better matching microwave energy to different tissue types and sizes.

In addition to the varying dielectric properties of the dielectric compounds, the flexible nature of the sheath 516 also provides for dynamic impedance matching by varying the amount of dielectric material "M" filling the lumen 528. The varying amount of the dielectric material "M" affects the bulk impedance of the antenna assembly 500 based on: (1) the amount of the dielectric material "M" present and (2) the dimension of the sheath 516, which is also based on the amount of the dielectric material "M" present therein.

Based on the dielectric constant of the material, the amount of the dielectric material "M" may be used to increase or decrease the dielectric permittivity of the antenna assembly 500. More specifically, if a dielectric material "M" having a dielectric constant of 2 or more is used then increasing the amount of the material within the lumen 528 reduces the effectiveness of microwave transmission. If a dielectric material "M" having a dielectric constant of 1 or less is used then increasing the amount of such material within the lumen 528 increases the effectiveness of microwave transmission.

The dielectric material "M" may also be used to vary dielectric permittivity of the sheath 516. As shown in FIGS. 11 and 12, the thickness of the sheath 516 varies based on the pressure within the lumen 528 (e.g., amount of the dielectric "M" present therein). Under lower pressure, as illustrated in FIG. 11, the sheath 516 has a relatively large thickness $w_1$. The elasticity of the sheath causes contraction, which increases the wall thickness $w_1$ resulting in a higher overall dielectric constant of the sheath 516. Under higher pressure, as illustrated in FIG. 12, the sheath has a thinner thickness $w_2$. Increasing the pressure within the lumen 528 expands the sheath 516, thereby decreasing the wall thickness $w_2$ while reducing the overall dielectric constant of the sheath 516.

Figure 13:
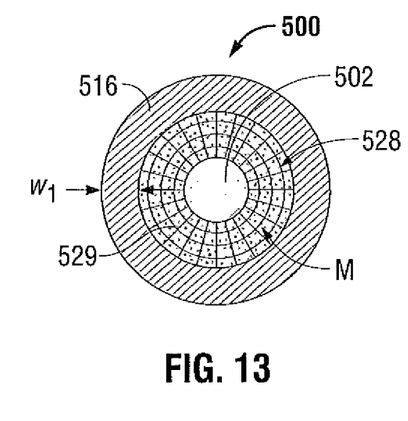
FIG. 13 is a cross-sectional view of another embodiment of a microwave antenna assembly in a deflated configuration according to an embodiment of the present disclosure.
Figure 14:
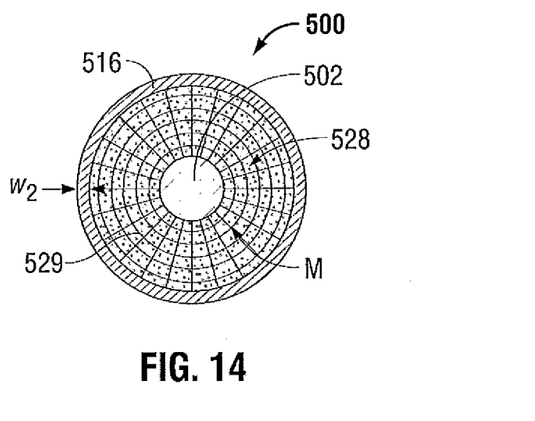
FIG. 14 is a cross-sectional view of the microwave antenna assembly of FIG. 13 in an inflated configuration according to an embodiment of the present disclosure.

FIGS. 13 and 14 illustrate another embodiment of the antenna assembly 500 having the expandable sheath 516. In particular, the antenna assembly 500 includes a dielectric permeable core 529 within the lumen 528. The core 529 may be formed from any suitable fibrous or porous dielectric material which may be permeable to the dielectric material "M" (e.g., sponge, fiberglass mesh, etc.). The core 529 is secured to the inner conductor 502 and the inner surface of the sheath 516, such that as the sheath 516 is deflated and inflated, the core 529 expands and contracts accordingly, as shown in FIGS. 13 and 14, respectively.

The core 529 provides structural integrity to the antenna assembly 500 by securing the inner conductor 512 at the center of the sheath 516. In addition, the dielectric material of the core 529 provides additional dielectric matching capabilities to the antenna assembly 500. The porous and/or fibrous structure of the core 529 allows the thickness of the sheath 516 to be varied as discussed above with respect to FIGS. 11 and 12. In particular, the thickness of the sheath 516 varies based on the pressure within the lumen 528 (e.g., amount of the dielectric "M" present therein). Under lower pressure, as illustrated in FIG. 13, the sheath 516 has a relatively large thickness $w_1$. The elasticity of the sheath causes contraction, which increases the wall thickness $w_1$ resulting in a higher overall dielectric constant of the sheath 516. In the deflated configuration, the core 529 in combination with the thickened sheath 516 act as the primary dielectric buffers. Thus, the core 529 may be formed from a dielectric material that is suitable for impedance matching the antenna assembly 500 in the deflated state.

Under higher pressure, as illustrated in FIG. 14, the sheath has a thinner thickness $w_2$. Increasing the pressure within the lumen 528 expands the sheath 516, thereby decreasing the wall thickness $w_2$ while increasing the volume of the lumen 528. This, in turn, reduces the overall dielectric constant of the sheath 516.

Figure 15:
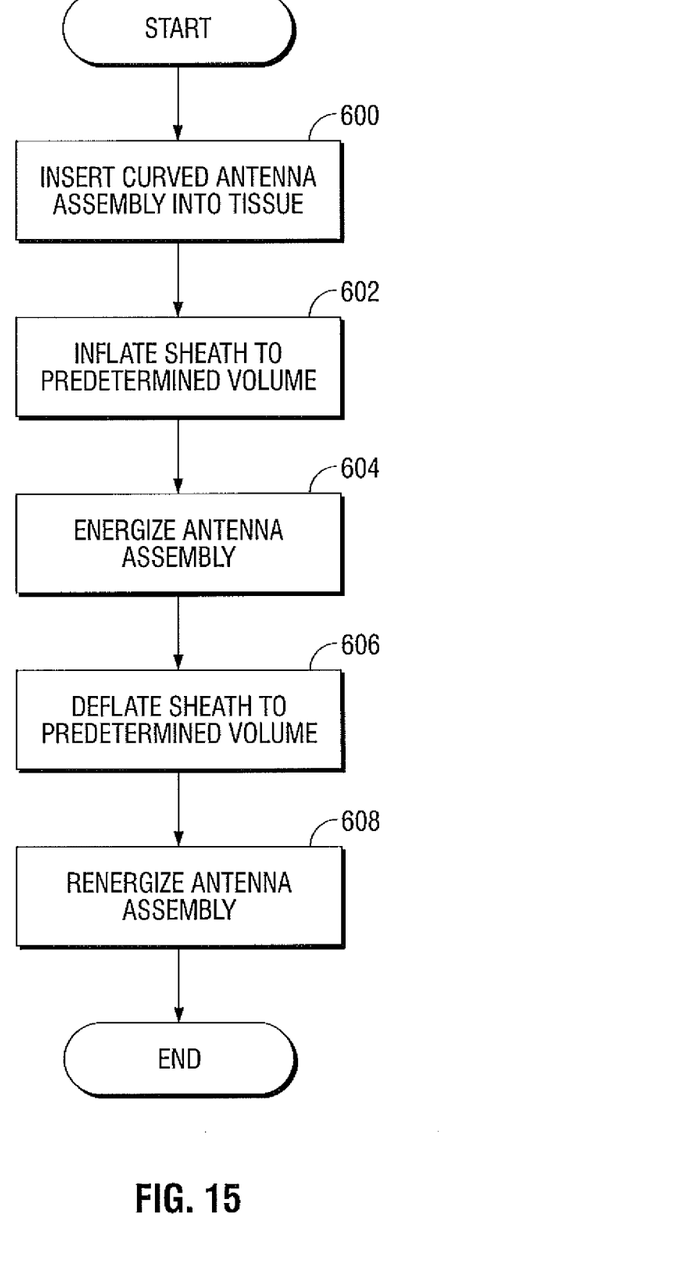
FIG. 15 is a flow chart of a method according to an embodiment of the present disclosure.

FIG. 15 illustrates a flow chart of a method for varying the dielectric properties of the antenna assembly 500. In step 600, the antenna assembly 500 is inserted into tissue and is deployed to surround the tissue volume "T" as shown in FIG. 10. In step 602, the sheath 516 is inflated to a predetermined volume such the sheath 516 is stretched to the thickness $w_2$. The thinner thickness $w_2$ provides for a lower dielectric permittivity, thereby providing for optimum impedance matching with undesiccated tissue. In step 604, the antenna assembly 500 is energized to ablate the tissue volume "T." As a result of the energy application, the tissue volume "T" is desiccated and the impedance thereof increases accordingly. In step 606, the sheath 516 is deflated by withdrawing the dielectric material "M." As the sheath 516 is deflated, the pressure is decreased, increasing the thickness $w_1$ of the sheath 516, thereby increasing the dielectric constant of the sheath 516 to provide for better dielectric matching with desiccated tissue. During step 606, microwave energy may be continuously supplied to the antenna assembly 500. In step 608, additional microwave energy is supplied to the antenna assembly 500. Steps 606 and 608 may be repeated multiple times to provide for step-down adjustments of the dielectric permittivity of the antenna assembly 500.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave antenna assembly comprising:
   an elongated member defining a longitudinal axis and having proximal and distal ends;
   an outer conductor and an inner conductor each disposed within the elongated member and extending along the longitudinal axis, at least a portion of the inner conductor being deployable relative to the outer conductor; and
   an expandable sheath at least partially disposed about a distal portion of the inner conductor and defining at least one lumen configured to receive a supply of a dielectric material to expand the expandable sheath, the inner conductor having a hemi-spherical cross-section.

2. The microwave antenna assembly according to claim 1, wherein the distal portion of the inner conductor is configured to extend laterally relative to the longitudinal axis to define an arcuate profile.

3. The microwave antenna assembly according to claim 2, wherein the arcuate profile defines an ablation region that at least partially surrounds an area of tissue to be treated.

4. The microwave antenna assembly according to claim 3, wherein the distal portion of the inner conductor is disposed in contact with the expandable sheath and the at least one lumen defines a gap oriented toward the ablation region.

5. The microwave antenna assembly according to claim 1, further comprising a dielectric permeable core disposed within the at least one lumen, the dielectric permeable core coupled to the inner conductor and an inner surface of the expandable sheath and configured to expand by absorbing the dielectric material delivered to the at least one lumen.

6. The microwave antenna assembly according to claim 5, wherein the dielectric permeable core comprises a sponge.

7. The microwave antenna assembly according to claim 1, wherein the dielectric material is selected from the group consisting of water, saline, chlorodifluoromethane, nitrogen, nitrous oxide, carbon dioxide, and mixtures thereof.

8. A microwave ablation system, comprising:
   an antenna assembly including:
     an elongated member defining a longitudinal axis and having proximal and distal ends;
     an outer conductor and an inner conductor each disposed within the elongated member and extending along the longitudinal axis, the inner conductor having a hemi-spherical cross-section, at least a portion of the inner conductor being deployable relative to the outer conductor; and
     an expandable sheath at least partially disposed about a distal portion of the inner conductor, the sheath defining at least one lumen configured to receive a dielectric material to expand the expandable sheath; and
   a fill source coupled to the at least one lumen and configured to control delivery of the dielectric material to the at least one lumen.

9. The microwave ablation system according to claim 8, wherein the distal portion of the inner conductor is configured to extend laterally relative a longitudinal axis of the outer conductor to define an arcuate profile.

10. The microwave ablation system according to claim 9, wherein the arcuate profile defines an ablation region that at least partially surrounds an area of tissue to be treated.

11. The microwave ablation system according to claim 10, wherein the distal portion of the inner conductor is disposed in contact with the expandable sheath and the at least one lumen defines a gap oriented toward the ablation region.

12. The microwave ablation system according to claim 8, wherein the distal portion of the inner conductor is disposed in contact with an outer side of the expandable sheath and the at least one lumen includes a gap defined therein between a surface of the distal portion of the inner conductor and an inner side of the expandable sheath, the gap oriented to direct microwave energy toward the ablation region.

13. The microwave ablation system according to claim 8, further comprising a dielectric permeable core disposed within the at least one lumen, the dielectric permeable core coupled to the inner conductor and an inner surface of the expandable sheath and configured to expand by absorbing the dielectric material delivered to the at least one lumen.

14. The microwave ablation system according to claim 13, wherein the dielectric permeable core comprises a sponge.

15. The microwave ablation system according to claim 8, wherein the dielectric material is selected from the group consisting of water, saline, chlorodifluoromethane, nitrogen, nitrous oxide, carbon dioxide, and mixtures thereof.

16. A method for performing microwave ablation, the method comprising:
   inserting an antenna assembly into a tissue volume, the antenna assembly including an outer conductor, an inner conductor having a hemi-spherical cross-section, and an expandable sheath at least partially disposed about a distal portion of the inner conductor and defining at least one lumen configured to receive a dielectric material;
deploying at least a portion of the inner conductor from the outer conductor;
delivering the dielectric material to the at least one lumen to expand the expandable sheath;
energizing the antenna assembly to ablate tissue; and
withdrawing the dielectric material from the at least one lumen to contract the expandable sheath.

17. The method according to claim 16, wherein deploying at least a portion of the inner conductor from the outer conductor includes extending the distal portion of the inner conductor laterally relative to a longitudinal axis of the outer conductor to define an arcuate profile.

18. The method according to claim 16, wherein the at least one lumen defines a gap oriented toward the ablation region.

19. The method according to claim 16, wherein the antenna assembly includes a dielectric permeable core disposed within the at least one lumen, the dielectric permeable core coupled to the inner conductor and an inner surface of the expandable sheath and configured to expand by absorbing the dielectric material delivered to the at least one lumen.

20. The method according to claim 19, wherein the dielectric permeable core comprises a sponge.

* * * * *